United States Patent

Gerstel

Patent Number: 4,883,504
Date of Patent: Nov. 28, 1989

[54] GAS CHROMATOGRAPH

[76] Inventor: Eberhard Gerstel, Heerstr. 4, D-4330 Mülheim a.d. Ruhr 14, Fed. Rep. of Germany

[21] Appl. No.: 196,362

[22] Filed: May 20, 1988

[30] Foreign Application Priority Data

May 23, 1987 [DE] Fed. Rep. of Germany ....... 3717456

[51] Int. Cl.$^4$ ............................................. B01D 15/08
[52] U.S. Cl. .......................................... 55/67; 55/197; 55/386
[58] Field of Search ............................ 55/67, 197, 386

[56] References Cited

U.S. PATENT DOCUMENTS

| | | | |
|---|---|---|---|
| 3,201,922 | 8/1965 | Villalobos | 55/67 |
| 3,357,233 | 12/1967 | Roof | 55/386 X |
| 3,364,659 | 1/1968 | Pierrard et al. | 55/386 X |
| 3,458,437 | 7/1969 | Ouano | 55/386 X |
| 3,518,059 | 6/1970 | Levy | 55/67 X |
| 3,524,305 | 8/1970 | Ives | 55/386 |
| 3,527,567 | 9/1970 | Philyaw et al. | 55/67 X |
| 3,557,533 | 1/1971 | Porter | 55/67 |
| 3,728,845 | 4/1973 | Haruki et al. | 55/67 |
| 3,992,175 | 11/1976 | Klementi et al. | 55/67 |
| 4,038,053 | 7/1977 | Golay | 55/67 X |
| 4,083,702 | 4/1978 | Hartigan et al. | 55/67 |
| 4,204,952 | 5/1980 | Snyder | 55/67 X |
| 4,230,464 | 10/1980 | Bonmati et al. | 55/67 X |
| 4,478,720 | 10/1984 | Perrut | 55/67 X |
| 4,617,032 | 10/1986 | Wells | 55/67 |
| 4,732,581 | 3/1988 | Cheh et al. | 55/67 |

FOREIGN PATENT DOCUMENTS

| | | | |
|---|---|---|---|
| 2448923 | 4/1975 | Fed. Rep. of Germany | 55/67 |
| 3400458 | 4/1987 | Fed. Rep. of Germany | |
| 1214627 | 12/1970 | United Kingdom | 55/67 |

OTHER PUBLICATIONS

Siemens Aktiengesellschaft, "Mehrdimensionale Chromatographie: Sichromat 2, der GC mit Doppelofen", (Multidimensional Chromatography: Sichromat 2, the GC with a double oven).

*Primary Examiner*—Robert Spitzer
*Attorney, Agent, or Firm*—Frishauf, Holtz, Goodman & Woodward

[57] ABSTRACT

A gas chromatograph having a carrier gas feed for a pressure-controlled feeding of a carrier gas stream, which feed leads to a sample applicator having preliminary separation which is connected to a branch piece and the latter to a separation column. The branch piece additionally has a feed line for a regulated auxiliary gas stream, an outlet leading to a switchable valve arrangement, an outlet leading to a monitoring detector; and throughbore with a restrictor therein. A detector is optionally connected to the separation column. To make it possible to achieve flows which are virtually always the same in the sample applicator and in the separation column without carry-over when the state of operation is switched and so that a time control and also control according to peak detection is possible, the two outlets are arranged in the branch piece on the sample application side with respect to the restrictor, and the feed line for the auxiliary gas stream discharges on the separation column side with respect to the restrictor.

A process for separation by gas chromatography advantageously applies this gas chromatograph.

83 Claims, 2 Drawing Sheets

GAS CHROMATOGRAPH

BACKGROUND OF THE INVENTION

The present invention is related to a gas chromatographic technique involving a gas chromatograph and a utilizing it for separation by gas chromatography and, particular, providing an improvement which achieves flows the sample applicator and in the separation column that are substantially the same in the different states in which the chromatograph is operated so as to enable control based on peak detection as well as under time control.

As disclosed in a company brochure of Siemens Aktiengesellschaft "Mehrdimensionale Chromatographie: SICHROMAT 2, der GC mit Doppelofen" (Multidimensional chromatography: SICHROMAT 2, the GC with a double oven), Order No. A19100-E687-A2-V1, a gas chromatograph incorporates a complicated branch piece. This component contains a long capillary, involves three different switching states, and requires two auxiliary gas flows regulated in different ways and exhibiting a differential pressure. In addition, although a monitoring detector is used, it is fed in only one of the three switching states and, thus, does not receive the entire chromatogram. Consequently, the chromatograph can only be switched based on time control, but not according to peak detection. Also, different flow conditions arise in the pre-column and the main column upon switching from one state to another. Such different flow conditions lead to an alteration of the retention times, thereby making adjustment of the time control difficult and time consuming. Moreover, intermediate cutting out can be achieved only at additional expense.

SUMMARY OF THE INVENTION

The primary object of the present invention is to provide a gas chromatograph technique with maintains virtually the same flows in the sample applicator and in the separation column in the different switched states.

Another object of the present invention is to provide a gas chromatograph technique in which there is practically n delay during switching between different operating states, and with practically no sample components being displaced during such switching.

A further object of the present invention is to provide a gas chromatograph technique which enables switching between operating modes on the time control as well as based on peak detection.

These and other objects are attained in accordance with one aspect of the present invention are attained by: a gas chromatograph comprising: a carrier gas inlet; a branch piece with a bore therethrough, and having first and second openings to the bore and first, second and third outlets from the bore; a first feed line coupled between the carrier gas inlet and the first opening of the branch piece; a sample applicator in the first feed line; a second feed line coupled between the carrier gas inlet and the second opening of the branch piece; a separation column in fluid communication with the first outlet; a valve in fluid communication with the second outlet of the branch piece; a monitoring detector in fluid communication with the third outlet of the branch piece; and a flow restrictor in the bore of the branch piece, one side of the restrictor having a section of the bore including the first opening and the second and third outlets, and another side of the restrictor having a section of the bore including the first outlet and the second opening.

Another aspect of the present invention is directed to a branch piece for a gas chromatograph comprising: means defining a through bore; a first inlet adapted to communicate the bore with a carrier gas stream from a sample applicator; a first outlet adapted to communicate the bore with a separation column; a second inlet adapted to communicate the bore with an auxiliary gas stream; a second outlet adapted to communicate the bore with a switchable valve arrangement; a third outlet adapted to communicate the bore with a monitoring detector; a flow restrictor in the bore; wherein the second and third outlets are on the same side of the restrictor as the first inlet, and the second inlet and first outlet are on the other side of the restrictor.

Still another aspect of the present invention is directed to a gas chromatograph comprising: a sample feed line adapted to accommodate flow therethrough of a carrier gas and injected sample; an auxiliary feed line adapted to accommodate flow therethrough of only a carrier gas; a separation column; a monitoring detector; control means for, when in a first mode, (1) setting pressure in the auxiliary feed line to exceed pressure in the sample feed line, (2) directing only carrier gas from the auxiliary feed line to the separation column, and (3) directing the injected sample with carrier gas to the monitoring detector, and when in a second mode, (1) setting pressure in the sample feed line to exceed pressure in the auxiliary feed line, and (2) directing the injected sample with carrier gas to the monitoring detector and the separation column.

DETAILED DESCRIPTION OF THE PREFERRED EMBODIMENTS

Figure 1:
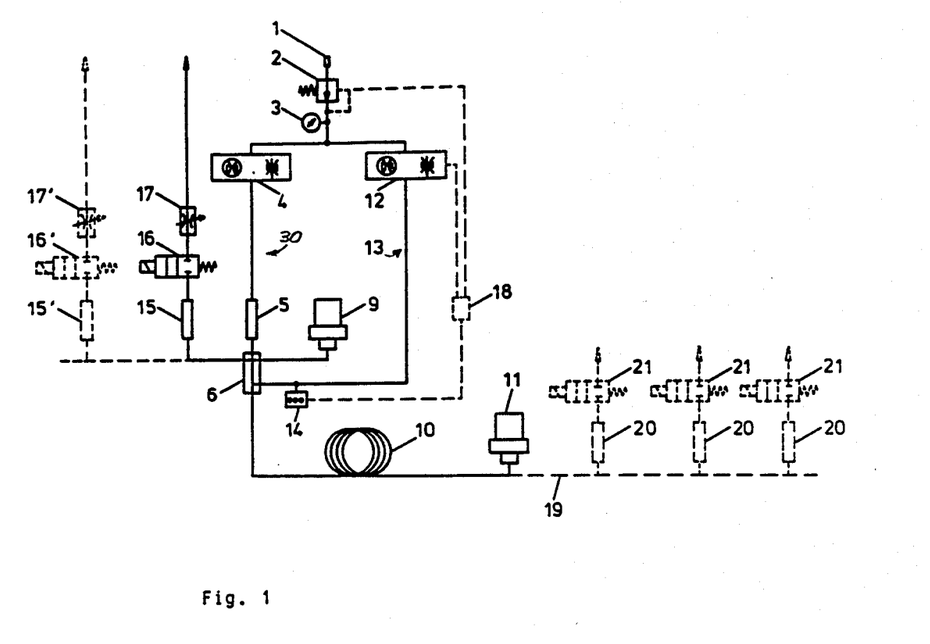
FIG. 1 is a schematic diagram showing the construction of the gas chromatograph of the present invention.

FIG. 1 shows a gas chromatograph having a carrier gas inlet 1. Carrier gas fed in through inlet 1 passes through a pressure controller 2. Manometer 3 positioned downstream of pressure controller 2 measures and displays the pressure of the carrier gas. The carrier gas stream then splits between a first flow branch 30 and a second flow branch 13. In the first flow branch 30, the flow level is selectively set by a flow controller 4 having a flow indicator. The carrier gas stream is fed to a sample applicator 5 which can be, for example, a cold applicator as disclosed in DE-OS No. 3,400,458 which is hereby incorporated by reference. It is noted that such a sample applicator produces a preliminary separation.

Figure 2A:
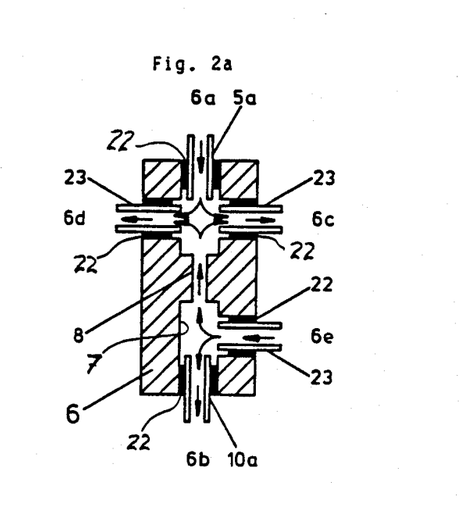
FIGS. 2a and 2b are sectional views of a branch piece for the gas chromatograph of FIG. 1 showing, respectively, the flow conditions through it in two operating states.
Figure 2B:
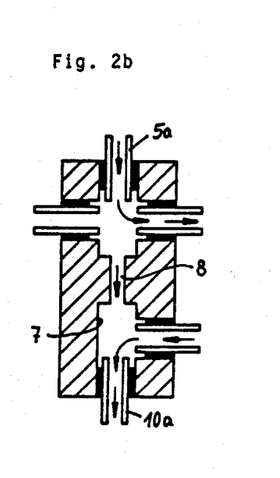

As shown in FIGS. 1, 2a and 2b, the outlet of sample applicator 5 is fed to inlet 6a of branch piece 6. Branch piece 6 has a throughbore 7 which extends from inlet 6a to an outlet 6b. A restrictor 8 is positioned in bore 7. Two outlets 6c and 6d branch off from bore 7 of the branch piece 6 in the region adjacent to inlet 6a, i.e. on the sample application side with respect to the restrictor 8. Outlet 6c leads to a monitoring detector 9 for determining a chromatogram. Outlet 6d of branch piece 6 is connected to a trap 15 having downstream therefrom a solenoid valve 16 and then a needle valve 17. Additional traps 15' having associated solenoid and needle valves 16', 17' (shown in FIG. 1 by broken lines) can optionally be connected parallel to the unit combining trap 15, solenoid valve 16 and needle valve 17. Outlet 6b of branch piece 6 is connected to a heatable chromatographic separation column 10, such as a capillary separation column. A packed separation column can also be used. Separation column 10 is connected to a principle detector 11.

In the second flow branch 13, a pressure-regulated carrier gas stream is fed as an auxiliary gas stream via a flow controller 12 provided with a flow level indicator. The auxiliary gas stream from flow controller 12 is supplied to inlet 6e of branch piece 6. Inlet 6e together with outlet 6b are located on the separation column side of bore 7 with respect to the restrictor 8. A digital manometer 14 is in fluid communication with the auxiliary gas stream between flow controller 12 and inlet 6e. Thus, the carrier gas stream is divided into two flow branches 13 and 30. The first flow branch feeds into branch 30 piece 6 via sample applicator 5, and is directed to outlets 6c and 6d of branch piece 6. The second flow branch 13 feeds an auxiliary gas stream to inlet 6e of branch piece 6.

The gas chromatograph described above has two operating states, or modes, which differ primarily with respect to whether solenoid valve 16 is open or closed and with respect to the flow level in the second flow branch 13. In the first operating state, the following conditions prevail: (a) solenoid valve 16 is maintained open so that fluid can flow through it from outlet 6d, (b) the auxiliary gas stream from the second flow branch 30 is set so as to be greater than the carrier gas stream in the first flow branch 13 to inlet 6a. As a result, some fluid, (a relatively small part of the auxiliary gas flow), flows through restrictor 8 from inlet 6e toward the sample application side of restrictor 8. This blocks flow of the carrier gas from sample applicator 5 through the restrictor and, consequently, to separation column 10. Flow of carrier gas from sample applicator 5 and second flow branch 13 reaches outlets 6c, to the monitoring detector 9, and through outlet 6d to trap 15 and valves 16 and 17 downstream thereof. With such an operating state being set, the following advantages are attained:

1. the monitoring detector 9 is fed with the entire chromatogram, 2. flow from outlet 6d can be used for cutting out (inter alia peak cutting, including hard cut) or for flushing trap 15 clean can readily be set at needle valve 17 so that it equals the differential flow rate in the second flow branch 13 between the first and second operating states, and 3. separation column 10 is supplied with gas flow such as is necessary, for example, to purge separation column 10 from a former sample simultaneously with cutting out of the present sample via outlet 6d being performed.

The following conditions prevail in the second operating state: (a) valve 16 is closed thereby shutting off flow through outlet 6d of branch piece 6, (b) flow from the sample applicator is redirected from outlet 6d through restrictor 8 to separation column 10, (c) the flow level from second flow branch 13 is reduced below the flow level of the fluid in the first flow branch 30, (d) and the difference in the flow levels of the second flow branch between the first and second states is set so as to be equal to the flow through needle valve 17. This setting can be accomplished by suitably adjusting one or more of flow controller 12, pressure regulator 2, and needle valve 17. Thus, the following advantages are attained.

1. flows in the sample applicator 5 and in the separation column 10 remain the same even when the chromatograph is switched from one operating state to another, 2. the second flow branch 13 is prevented from being contaminated by the present sample being processed due to the stream of auxiliary gas always flowing through it, and 3. monitoring detector 9 is continuously fed with the entire chromatogram.

It is essential for the proper working of the gas chromatograph of the present invention that the flows in sample applicator 5 and separation column 10 remain the same in both operating states despite switching from one to the other at whatever point in time this occurs. This is attained by ensuring that the flow at outlet 6d of branch piece 6 as set by needle valve 17, is equal to the difference between the streams of auxiliary gas through the second branch line 13 and two operating states, as set by flow control 12. Flow reversal upon switching over from one operating state to another is limited to the very short length of the flow restrictor 8 in branch piece 6 and, thus, has a minimal disturbing effect on the measurements. The differential flow levels in the second flow branch 13 between the two operating states is set by reading off the manometer 14 and by manual setting of flow controller 12. FIG. 1 shows in broken lines a set point adjuster 18 coupled to flow controller 12 and pressure regulator 2. Set point adjuster 18 is connected to manometer 14, and is capable of automatically setting the flow level in the second flow branch for both operating states.

Because monitoring detector 9 is constantly fed, it provides a complete chromatogram which enables operation based on peak detection in order to cut out the solvent, carry out intermediate or terminal cutting out (i.e., cutting out of the particular part of the chromatogram right down to an individual peak), or to flush clean without contamination. This is possible in addition to operation under time control. Since monitoring detector 9 is continuously fed by the carrier gas stream from sample applicator 5, corresponding peaks can be detected in accordance with the preliminary separation effected by sample applicator 5, and hence to cut them out by selecting the first operating state while the parts of the chromatogram which are of interest are fed to separation column 10 by suitably switching over to the second operating state.

Because equal flows are maintained in both operating states, no alterations in retention times result from the switch-over. Consequently, a switch-over from one operating state to the other can be carried out with reference to a fixed time program in order to perform the desired operations of cutting out and flushing clean after each sample application. Back flushing of sample operator 5 and a pre-column (if one is used - see below) is possible. To perform such back flushing, it is possible to add (although this is not shown in the drawings) an additional branch line 30 connected to the first branch line between control element 4 and sample applicator 5. This added branch line would have a solenoid and a needle valve corresponding to valves 16 and 17, respectively.

The two operating states of the gas chromatograph are suitable both for analytical and for preparative operation. For the latter, a preparative discharge 19 comprising one or more collectors 20 can be used at the outlet end of separation column 10. Each of collectors 20 can be selectively switched in temporarily via respective valves 21.

The gas chromatograph of the present invention makes it possible to perform a rapid sequence of sample injections since time cutting via outlet 6d and purging of the separation column 10 via outlet 6b can take place simultaneously in the first operating state. Furthermore, since the flow characteristics are set at the beginning in such a manner that they are practically unchanged in switching from one operation mode to the other, a time-consuming and troublesome setting during operation of the system is avoided.

The part of the chromatogram which has been cut out as per the above is not lost, but is caught in the trap 15 (and, if required, in further traps 15'). It is for this reason also, that it is possible, in the first operating state, to trap substances of no interest, such as solvents or the like, in the trap 15, (which here serves as a zero trap) and to trap or even enrich substances of interest in one or more traps 15' without using a capillary separation column 10 for this purpose and only by using the preliminary separation effected by the sample applicator 5. These substances of interest can subsequently be investigated further by means of the capillary separation column 10. Also, further cutting-out operations can be carried out. For this purpose, the trapped or enriched substances are introduced into the sample applicator 5. Since the traps 15, 15' usually have tubes which receive the substances fed in it is expedient to use an identical tube in the sample applicator 5 so that the latter can be replaced by that from the trap 15'. Thus, according to DE-OS No. 3,400,458, the cold applicator has a (heatable) vaporizer tube which, in such a case, can be replaced by an identical tube from a trap 15' having a corresponding content.

Although a cold applicator in accordance with DE-OS No. 3,400,458 is preferred for sample applicator 5, it is also possible to use one with a heatable pre-column.

Suitable detectors 9, 11 are, for example, flame ionization detectors, mass spectrometers or the like.

Massflow regulators can also be used instead of flow controllers 4, 12. It is moreover possible to use simple needle valves instead of controllers 4, 12 while the output of the manometer 14 regulates the pressure controller 2, such that control is carried out solely via the pressure.

According to FIGS. 2a, 2b, the end piece 5a of the sample applicator discharges in the bore 7, coaxially to the latter, and is sealed by means of a graphite seal 22. The connection pieces 23 for the monitoring detector 9 and the trap 15 likewise discharge in the bore 7, at right angles to the longitudinal axis of the latter, on one side of the restrictor 8, and first flow branch 13 discharges on the other side of the restrictor 8. The inlet piece 10a of the capillary separation column 10 is accommodated by the bore 7 in a manner coaxial to the bore 7. These parts too are sealed by graphite seals 22. The dimensioning of the restrictor 8 depends on the prevailing pressure and flow conditions. In the case of the use of a capillary separation column 10, the restrictor 8 can be formed by a bore of a diameter of the order of 0.2 mm and a length which is a small multiple of the diameter, and preferably is of the order of 0.7 mm. If required, the restrictor 8 can be formed by an insertion of inert material, such as an Si crystal, having a surface inactivated with oxygen, or glass, which is inserted into the branch piece 6. If required, the branch piece 6 can furthermore be heatable to prevent substances from condensing out therein. For this purpose, it is also possible to provide a thermally conductive, for example metallic, connection from the branch piece 6 to the sample applicator 5. All the connection pieces 5a, 10a, and 23 can be of glass so that, in particular, the transitions from the sample applicator 5 to the branch piece 6 and from there to the separation column 10 and the trap 15 are always of glass.

Figure 3:
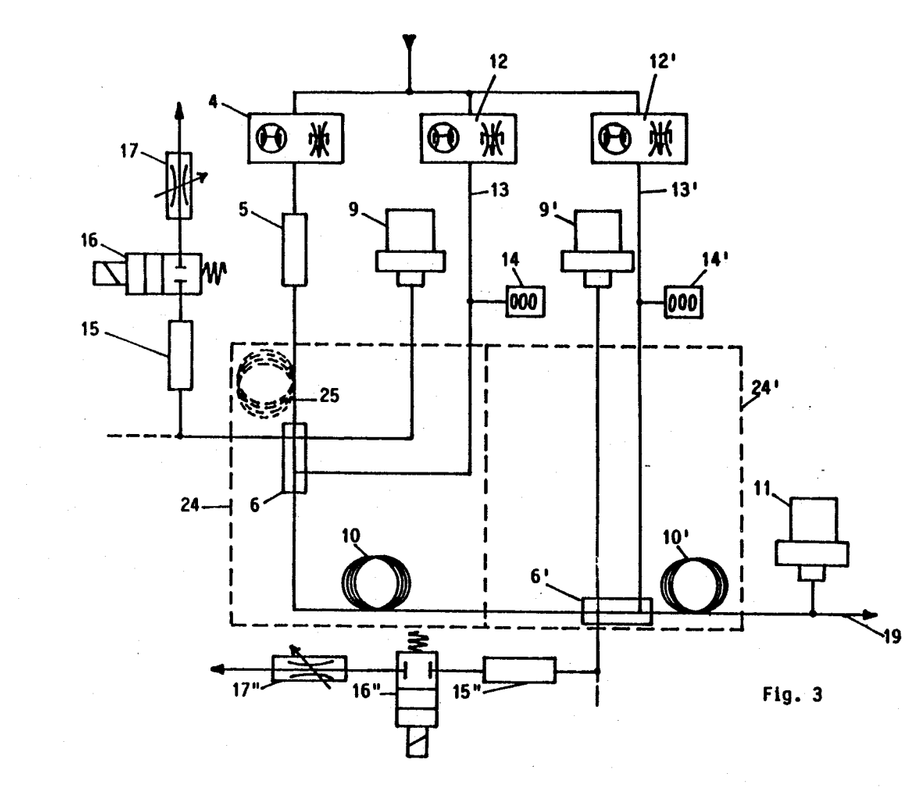
FIG. 3 is a schematic diagram of a second embodiment for the construction of a gas chromatograph in accordance with the present invention.

A second embodiment of a gas chromatograph arranged in accordance with the present invention is illustrated in FIG. 3. It differs from that shown in FIG. 1 in that, instead of one oven in which the branch piece 6 and the separation column 10 are arranged (not shown in FIG. 1), two ovens 24 and 24', connected in series, are provided. The outlet of the separation column 10 in the first oven 24 is connected via another branch piece 6' situated in the second oven 24' to another separation column 10' situated in the second oven 24'. Another monitoring detector 9', an auxiliary gas line 13' provided with a further flow controller 12', manometer 14' and one or more traps 15'' having associated solenoid and needle valves 16'' and 17'' are connected to the branch piece 6' in the same way as the corresponding parts are connected to branch piece 6. The outlet of separation column 10' is connected to the principal detector 11 and optionally to a preparative discharge 19. However, further ovens corresponding to oven 24', having corresponding monitoring detectors, auxiliary gas feeds and traps, which are connected to further branch pieces, and having further separation columns can also be provided.

The embodiment shown in FIG. 3 can be used to cut the chromatogram, if required a multiplicity of times, without splitting. In this arrangement, backflushing does not take place since parts which have been cut away are fed to the trap(s) 15'' via the branch piece 6'. This mode of operation is again made possible by flow monitoring.

An auxiliary separation column 25 can furthermore be provided downstream of the sample applicator 5 within the first oven 24 or outside the latter in an auxiliary oven which makes possible controllable and, optionally, programmable heating, in order to effect an appropriate preliminary separation.

The transfer lines to traps 15, 15', 15'' and to the preparative traps 20 are heatable.

If required, the sample applicator can be capable of being cooled with liquid nitrogen.

By, for example, the selection of an appropriate capillary diameter, the installation of a restrictor, or by the action of a pneumatic backpressure, the line leading from outlet 6c of a branch piece 6 or 6' to a monitoring detector 9 or 9' has a flow-restricting effect. The degree of flow-restricting effect is selected as a function of the resistance of the separation column 10 or 10' connected to the branch piece 6 or 6', such that preferably 1/500 to 1/1000 of the flow fed to the branch piece 6 or 6' is diverted to the monitoring detector 9 or 9' and hence the chromatogram is impaired as little as possible. The line between outlet 6c and the monitoring detector 9 or 9' is therefore to be chosen as a function of the capillary used for the separation column 10 or 10'.

In the embodiment of FIG. 3, the monitoring detector 9 may monitoring. The sample components leaving separation column 10 are then controlled by the monitoring detector 9' which is therefore used as a control means for the preliminary cutting which takes place at the branch piece 6. The same principle may be used in the case of further separation columns 10' so that the amount of detectors 9' is limited accordingly.

After leaving column 10 a further cut may take place in that both separation columns 10 and 10' are located in the same oven 24, i.e. oven 24 and 24' are connected to one oven in this case. This may be used for cutting off components which evaporate easily as well as those which are difficult to evaporate whereas components representing the middle part of the chromatogram remain for further handling, i.e. analyzing and/or trapping, etc.

After cutting, the remaining components may be focussed between two ovens 24, 24' for instance by cooling the branch piece 6' for a certain time interval. This will improve the chromatographic results.

The main cut should be done by a temperature programmed heating of the corresponding separation column through which the remaining sample components are conducted.

All parts of the gas chromatograph which were mentioned above without discussing the structure thereof are standard items. Consequently, no structural details thereof are deemed to be necessary.

Although the embodiments of the present invention have been disclosed in detail above, it should be apparent to anyone with ordinary skill in the art that a number of modifications thereto can readily be made. All such modifications are intended to fall within the scope of the present invention as defined by the following claims.

I claim:

1. A process for separation by gas chromatography, comprising the steps of:
   in a first operating state
   (a) passing a regulated carrier gas stream through a sample applicator,
   (b) directing a relatively small portion of flow from said sample applicator to a monitoring detector,
   (c) directing the remainder of flow from the sample applicator to an open discharge line,
   (d) blocking access to a separation column of flow from the sample applicator with a regulated auxiliary gas stream, and
   (e) directing at least the major portion of the regulated auxiliary gas stream to the separation column; and
   in a second operating state
   (a) closing the discharge line,
   (b) directing a relatively small portion of flow from said sample applicator to a monitoring detector,
   (c) directing the remainder of flow from the sample applicator, and all the regulated auxiliary gas stream, to said separation column, and
   (d) maintaining flow through the sample applicator and the separation column at substantially the same level as during the first operating state.

2. The process of claim 1, further comprising the step of cutting out part of the chromatogram through the discharge line in the first operating state.

3. The process of claim 2, wherein the cutting-out step comprises peak detection by said monitoring detector.

4. The process of claim 2, wherein the cutting-out step comprises time control.

5. The process of claim 2, further comprising the step of trapping the parts of the chromatogram which have been cut out.

6. The process of claim 5, further comprising the step of enriching the trapped parts of the chromatogram.

7. The process of claim 6, further comprising the step of feeding through the sample applicator the trapped parts of the chromatogram.

8. The process of claim 7, further comprising the step of feeding through the sample applicator the enriched parts of the chromatogram.

9. The process of claim 1, further comprising the steps of passing flow from the sample applicator through a plurality of separation columns in succession, and cutting out parts of the chromatogram between two successive separation columns.

10. The process of claim 9, further comprising the step of trapping the parts of the chromatogram cut out between successive separation columns.

11. A process for the separation of components of a sample by gas chromatography having two operating states which can be switched therebetween, comprising:
   in a first operating state, passing a regulated carrier gas stream together with components of said sample through a sample application means, and from there a main part of said stream to an opened discharge line means and a minor part of said stream to a monitoring detection means, and blocking the access to a separation column means for separating said components;
   in a second operating state, passing said regulated carrier gas stream together with components of said sample on to said separation column means by closing said discharge line means, flow of said minor part of said carrier gas stream to said monitoring detection means of said first operating state being continued;
   maintaining constant the carrier gas flows into said sample application means and said separation column means during said first and second operating state.

12. The process of claim 11, wherein, in said first operating state, cutting out parts of the components of said sample via said discharge line means.

13. The process of claim 12, wherein said cutting out is effected via a peak detection by said monitoring detection means.

14. The process of claim 12, wherein said cutting out is effected via a time control.

15. The process of claim 12, wherein parts of said components of said sample which have been cut out are trapped and further comprising means for optionally enriching said trapped components.

16. The process of claim 15, wherein said trapped components are fed in through said sample application means and are passed through said separation column means except those components which may have been cut out before reaching said separation column means.

17. The process of claim 11, wherein said carrier gas stream containing said sample components is passed through at least two separation column means in succession, parts of said sample components being discharged at a location between two succeeding separation column means by using a regulated auxiliary carrier gas stream, said monitoring detection means being provided with a minor part of said carrier gas stream from a location between two separation column means.

18. The method of claim 17, wherein said sample components leaving one separation column means are focussed by cooling a connection to a succeeding separation column means.

19. A gas chromatographic system comprising:
a carrier gas supply means for a pressure regulated supply of a carrier gas stream to the system;
a sample application means for the introduction of a sample to be chromatographically handled into the system, said sample application means being able to provide a preliminary chromatographic separation of said sample and being connected with said carrier gas supply means so that a first stream of carrier gas can flow through said sample application means;
a branching means which is provided with two inlet means and at least two outlet means, a first one of said inlet means being connected with said sample application means, a first one of said outlet means being connected with a separation column means and said first inlet and outlet means being connected with each other via a conduit means provided with a throttle means, the second inlet means being connected with said carrier gas supply means for the supply of a regulated second auxiliary carrier gas stream to said conduit means at a location between said first outlet means and said throttle means, and the second outlet means being connected with a switchable valve arrangement and further with said conduit means at a location between said first inlet means and said throttle means; and
two operating states, in the first one of which said valve arrangement is open so that said second auxiliary stream of carrier gas prevents the introduction of incoming components of said sample into said separation column, whereas in the second one of which said valve arrangement is closed so that said incoming components of said sample are introduced into said separation column.

20. The system of claim 19, wherein said branching means is provided with a third outlet means which is connected with said conduit means at a location between said first inlet means and said throttle means, and further with a monitoring detector means so that in said both operating states said monitoring detector is fed with the whole incoming components of said sample.

21. The system of claim 19, wherein a control means for adjusting said first gas stream is provided.

22. The system of claim 19, wherein said first and said second gas streams are regulated by flow control means.

23. The system of claim 22, wherein said flow control means are mass flow controllers.

24. The system of claim 19, wherein between said carrier gas supply means and said second inlet means a line means is provided which contains a pressure gauge means upstream of said branching means.

25. The system of claim 24, wherein the output of said pressure gauge means is used to control a control element including means for adjusting said auxiliary gas stream.

26. The system of claim 25, wherein the output of said pressure gauge means is used to control the carrier gas feed of said carrier gas supply means.

27. The system of claim 24, wherein needle valve means are used as control elements, an output of said pressure gauge means controlling a pressure controlling means of said carrier gas supply means.

28. The system of claim 24, wherein an output of said pressure gauge means is used to control the carrier gas feed of said carrier gas supply means.

29. The system of claim 19, wherein said valve arrangement comprises an adjustable needle valve means.

30. The system of claim 19, wherein a trap means is connected upstream of said valve arrangement.

31. The system of claim 30, wherein said trap means has a collecting tube means which is identical to and interchangeable with a vaporizer tube means of said sample application means.

32. The system of claim 19, wherein a plurality of units which can be opened and closed independently of one another by valve means and in each case comprise a trap means and a switchable valve arrangement are connected in parallel to the said second outlet means of said branching means.

33. The system of claim 32, wherein said trap means has a collecting tube means which is identical to and interchangeable with a vaporizer tube means of said sample application mean.

34. The system of claim 19, wherein said branching means is heatable.

35. The system of claim 19, wherein said branching means is in thermally conductive connection with said sample application means.

36. The system of claim 19, wherein at least one further separation column means is provided which is connected via a further branching means to a preceding separation column, said further branching means being provided with two inlet means and three outlet means, a first one of said inlet means being connected with said preceding separation column, a first one of said outlet means being connected with said further separation column and said first inlet and outlet means being connected with each other via a further conduit means provided with a further throttle means, the second outlet means being connected with one or more further switchable valve arrangements and with said further conduit means at a location between said first inlet means and said further throttle means, said second inlet means being connected with said carrier gas supply means for the supply of a regulated further auxiliary carrier gas stream to said further conduit means at a location between said first outlet means and said throttle means, and said third outlet means being connected with said further conduit means at a location between said first inlet means and said throttle means and further with a monitoring detector means.

37. The system of claim 36, wherein a separate oven means is provided for each separation column means.

38. The system of claim 36, wherein an oven means is provided for at least two separation column means.

39. The system of claim 19, wherein an auxiliary separation column means is connected upstream of said branching means.

40. A gas chromatograph comprising:
a carrier gas inlet;
a branch piece with a bore therethrough, and having first and second openings to the bore and first, second and third outlets from the bore;

a first feed line coupled between the carrier gas inlet and the first opening of said branch piece;

a sample applicator in said first feed line;

a second feed line coupled between the carrier gas inlet and the second opening of said branch piece;

a separation column in fluid communication with the first outlet;

a valve in fluid communication with the second outlet of said branch piece;

a monitoring detector in fluid communication with the third outlet of said branch piece; and a flow restrictor in said bore of the branch piece, one side of the restrictor having a section of the bore including said first opening and said second and third outlets, and another side of the restrictor having a section of the bore including the first outlet and the second opening.

41. The gas chromatograph of claim 40, further comprising means for adjusting flow in the second feed line.

42. The gas chromatograph of claim 41, further comprising control means for, in a first mode, maintaining the valve open and for setting the adjustment means to a first flow level and, in a second mode, closing said valve and setting the adjustment means to a second flow level, said second flow level being less than the first flow level by an amount substantially equal to flow through said valve in the first mode 43. The gas chromatograph of claim 42, wherein the flow through the first feed line in both modes is less than said first level and more than said second level.

44. The gas chromatograph of claim 43, further comprising a pressure gauge in the second feed line upstream of the branch piece, said control means being responsive to an output of the pressure gauge.

45. The gas chromatograph of claim 44, further comprising pressure controller in fluid communication between the carrier gas inlet and the second feed line, said pressure controller being coupled to the pressure gauge.

46. The gas chromatograph of claim 45, further comprising means for adjusting fluid flow in the first feed line.

47. The gas chromatograph of claim 46, further comprising means for adjusting fluid flow through the valve.

48. The gas chromatograph of claim 47, further comprising a trap upstream of said valve.

49. The gas chromatograph of claim 48, further comprising a plurality of units connected in parallel to the trap and the valve and coupled to the second output, each of said units comprising a said trap and a said valve, said control means operating the units independently of each other.

50. The gas chromatograph of claim 49, wherein the sample applicator includes a vaporizer tube and said trap includes a collecting tube identical to and interchangeable with said vaporizer tube.

51. The gas chromatograph of claim 50, wherein said branch piece is of a heatable type.

52. The gas chromatograph of claim 51, wherein the branch piece is in thermally conductive connection with the sample applicator.

53. The gas chromatograph of claim 52, further comprising a controllably heated auxiliary separation column between the branch piece and the sample applicator.

54. The gas chromatograph of claim 53, further comprising a further separation column in fluid communication through a further branch piece to said separation column, a further valve in fluid communication with a second outlet of the further branch piece, and a second opening of the further branch piece being in fluid communication with a third feed line coupled to the carrier gas outlet, and a further monitoring detector coupled to a third output of the further branch piece.

55. The gas chromatograph of claim 54, further comprising a further trap coupled upstream of the further valve.

56. The gas chromatograph of claim 40, wherein the sample applicator includes a vaporizer tube and said trap includes a collecting tube identical to and interchangeable with said vaporizer tube.

57. The gas chromatograph of claim 40, wherein said branch piece is of the heatable type.

58. The gas chromatograph of claim 40, further comprising means for providing a thermally conductive connection between the branch piece and the sample applicator.

59. The gas chromatograph of claim 40, further comprising a controllably heated auxiliary separation column between the branch piece and the sample applicator.

60. The gas chromatograph of claim 40, further comprising a further separation column in fluid communication through a further branch piece to said separation column, a further valve in fluid communication with a second outlet of the further branch piece, and a second opening of the further branch piece being in fluid communication with a third feed line coupled to the carrier gas outlet, and a further monitoring detector coupled to a third output of the further branch piece.

61. The gas chromatograph of claim 60, comprising a further trap coupled upstream of the further valve.

62. A gas chromatograph comprising:

a sample feed line adapted to accommodate flow therethrough of a carrier gas and injected sample;

an auxiliary feed line adapted to accommodate flow therethrough of only a carrier gas;

a separation column;

a monitoring detector;

control means for, when in a first mode, (1) setting pressure in the auxiliary feed line to exceed pressure in the sample feed line, (2) directing only carrier gas from the auxiliary feed line to the separation column, and (3) directing the injected sample with carrier gas to the monitoring detector, and when in a second mode, (1) setting pressure in the sample feed line to exceed pressure in the auxiliary feed line, and (2) directing the injected sample with carrier gas to the monitoring detector and the separation column.

63. The gas chromatograph of claim 62, wherein the control means comprises means for regulating flow through the sample applicator to be substantially unchanged in both the first and second modes.

64. The gas chromatograph of claim 63, wherein the control means comprises means for regulating fluid flow to the separation column to be substantially constant in both the first and second modes.

65. The gas chromatograph of claim 64, further comprising a valve, and wherein said control means includes valve control means for holding said valve open in the first mode, and for holding said valve closed in the second mode, said control means directing flow of injected sample and carrier gas to the valve in said first mode.

66. The gas chromatograph of claim 65, wherein the regulating means comprises flow control means for decreasing flow of carrier gas in the auxiliary feed line in the second mode relative to the first mode by an amount substantially equal to flow of the injected sample and carrier gas through said valve in the first mode.

67. The gas chromatograph of claim 66, further comprising a trap connected upstream of said valve.

68. The gas chromatograph of claim 65, further comprising a trap connected upstream of said valve.

69. The gas chromatograph of claim 62, wherein the control means comprises means for regulating fluid flow to the separation column to be substantially constant in both the first and second modes.

70. The gas chromatograph of claim 62, further comprising a valve, and wherein said control means includes valve control means for holding said valve open in the first mode, and for holding said valve closed in the second mode, said control means directing flow of injected sample and carrier gas to the valve in said first mode.

71. The gas chromatograph of claim 70, wherein the control means comprises flow control means for decreasing flow of carrier gas in the auxiliary feed line in the second mode relative to the first mode by an amount substantially equal to flow of the injected sample and carrier gas through said valve in the first mode.

72. A branch piece for a gas chromatograph comprising:
means defining a through bore;
a first inlet adapted to communicate said bore with a carrier gas stream from a sample applicator;
a first outlet adapted to communicate said bore with a separation column;
a second inlet adapted to communicate said bore with an auxiliary gas stream;
a second outlet adapted to communicate said bore with a switchable valve arrangement;
a third outlet adapted to communicate said bore with a monitoring detector;
a flow restrictor in said bore;
wherein the second and third outlets are on the same side of the restrictor as the first inlet, and the second inlet and first outlet are on the other side of said restrictor.

73. The branch piece of claim 72, wherein the restrictor comprises a constriction of the through bore of the branch piece of small diameter, and of a length which is a multiple of the diameter.

74. The branch piece of claim 73, wherein the diameter of the restrictor is of the order of 0.2 mm, and the length is a small multiple thereof.

75. The branch piece of claim 72, wherein the through bore contains an insert which has the restrictor.

76. The branch piece of claim 72, wherein the insert is composed of an inert material, in particular an Si crystal whose surface has been inactivated with oxygen, or of glass.

77. The branch piece of claim 72, wherein said branch piece is heatable.

78. A branch piece for a gas chromatographic system, comprising a through bore means provided with a throttle means, with a first inlet means for a first carrier gas stream and components of a sample to be handled chromatographically and carried with said first carrier gas stream and with a first outlet means to a separation column; a second inlet means for the supply of a regulated second auxiliary carrier gas stream to said through bore at a location between said first outlet means and said throttle means, a second outlet means for the connection of one or more switchable valve arrangements and provided at a location between said first inlet means and said throttle means, and a third outlet means at a location between said first inlet means and said throttle means for the connection of a monitoring detection means.

79. The branch piece of claim 78, wherein said throttle means comprises a constriction of said through bore of small diameter and a length which is a multiple of said diameter.

80. The branch piece of claim 79, wherein said diameter of said throttle means is in the order of magnitude of 0.2 mm and said length is a small multiple thereof.

81. The branch piece of claim 78, wherein said through bore means contains an insert means which is provided with said throttle means.

82. The branch piece of claim 81, wherein said insert means is composed of an inert material.

83. The branch piece of claim 78, further comprising a heating means.

* * * * *

UNITED STATES PATENT AND TRADEMARK OFFICE
CERTIFICATE OF CORRECTION

PATENT NO. : 4,883,504
DATED : November 28, 1989
INVENTOR(S) : Eberhard GERSTEL

It is certified that error appears in the above-identified patent and that said Letters Patent is hereby corrected as shown below:

Column 8, claim 16 (line 4), delete "may".

Column 9, claim 25 (line 1), change "the" after "wherein" to -- an --.

Column 11, claim 45 (line 2), before "pressure" insert -- a --.

Column 12, claim 56 (line 1), before "wherein", insert -- further comprising a trap upstream of said valve, and --.

Signed and Sealed this

Thirteenth Day of August, 1991

Attest:

HARRY F. MANBECK, JR.

*Attesting Officer*   *Commissioner of Patents and Trademarks*